(12) United States Patent
Garay-Rodriguez et al.

(10) Patent No.: US 8,084,396 B2
(45) Date of Patent: Dec. 27, 2011

(54) AQUEOUS COMPOSITION FOR THE PROTECTION AND STRENGTHENING OF PLANTS AND APPLICATION METHOD THEREOF

(75) Inventors: Benjamin Garay-Rodriguez, Zapopan (MX); Dionicio Urbina-Lopez, Guadalajara (MX); Jose Manuel Rodriguez-Dominguez, Guadalajara (MX)

(73) Assignee: Centro de Investigacion y Asistencia en Technologia y Diseno del Estado de Jalisco A.C., Guadalajara, Jalisco (MX)

( * ) Notice: Subject to any disclaimer, the term of this patent is extended or adjusted under 35 U.S.C. 154(b) by 1056 days.

(21) Appl. No.: 11/722,069

(22) PCT Filed: Dec. 13, 2005

(86) PCT No.: PCT/MX2005/000115
§ 371 (c)(1),
(2), (4) Date: Dec. 4, 2007

(87) PCT Pub. No.: WO2006/078152
PCT Pub. Date: Jul. 27, 2006

(65) Prior Publication Data
US 2008/0119360 A1 May 22, 2008

(30) Foreign Application Priority Data
Dec. 17, 2004 (MX) ............... JL/A/2004/000049

(51) Int. Cl.
*A01N 43/02* (2006.01)
(52) U.S. Cl. ............................................... 504/140
(58) Field of Classification Search ............... None
See application file for complete search history.

(56) References Cited

FOREIGN PATENT DOCUMENTS

| SU | 1153403 | * | 2/1996 |
| WO | WO9103159 | * | 3/1991 |
| WO | WO9624246 | * | 8/1996 |

OTHER PUBLICATIONS

Krinsky, Non-photosynthetic functions of carotenoids, Phil Trans R Soc Lond B 284: 581-590 (1978).*
Leustek et al., The influence of glutamine on growth and viability of cell suspension cultures of Douglas-fir after exposure to polyethylene glycol, Tree Physiol 4: 371-38- (1988).*

* cited by examiner

*Primary Examiner* — Johann Richter
*Assistant Examiner* — Thor Nielsen
(74) *Attorney, Agent, or Firm* — Defillo & Associates, Inc.; Evelyn A. Defillo

(57) ABSTRACT

It is described an aqueous composition for the protection and strengthening of plants comprising: polyethylene glycol in a concentration of 2.0 to 10.0 grams per liter of the composition, wherein the polyethylene glycol has a molecular weight of 6000 to 8000 grams/mol; vitamin A or a derivative or precursor thereof, including mixtures of same, in a concentration of 0.1 to 10.0 grams per liter of composition, and, at least a red coloring agent in a concentration of 0.1 to 10.0 grams per liter of composition, wherein said colorant enables the passage of light at wavelengths greater than 600 nanometers. The aqueous composition is very useful to prevent biotic or abiotic factors generating stress in plants, as well as for quickly improving plants that are in this state. In an embodiment of the invention, the aqueous composition comprises at least one glucoside; and/or at least a foliar fertilizer. In addition, it is described the application method for the composition.

13 Claims, 3 Drawing Sheets

AQUEOUS COMPOSITION FOR THE PROTECTION AND STRENGTHENING OF PLANTS AND APPLICATION METHOD THEREOF

TECHNICAL FIELD

The present invention relates to the techniques used in the agriculture industry and gardening for the obtainment and manufacturing of compositions useful in cultures, management and caring of plants, and more particularly, it is related to an aqueous composition for the protection and strengthening of plants as well as to the application method thereof.

BACKGROUND OF THE INVENTION

As it is well known, plants suffer of several types of biotic or abiotic stress reducing their vitality and some times provoking the death of the plants.

For example, in the micro-propagation biotechnological processes, the plants become dehydrated and photo-oxidized due to a sudden light excess and intensity received by the plant when from an in vitro condition goes through an adaptation phase to the ex vitro life, i.e., in the micro-propagation, the plants suffer a sudden change of light conditions, and in the ex vitro phase are positioned in a soil located in any type of container. In addition, through all the ex vitro adaptation phase and up to the plants being capable to their transplanting in the final destination, the plants are exposed to stress conditions. Moreover, in said transplanting the plants suffer a very important dehydrating stress due to the sudden changes in going to a lower relative humidity conditions compared to the inside in vitro conditions.

Similarly, the same problem is observed in the small leaf clusters obtained by conventional germination systems or by cuttings obtained in greenhouses. In this regard, a good health plant has a higher commercial value than one stressed, being this an important factor for the survival of the field vegetables.

Regarding the dehydration, it is worth mentioning that this phenomenon may also be caused by a lack of watering or by the high speed winds, which make the plants to loss water through the leaves. Moreover, it is worth to remember that the plants transpire water through their leaves due to the photosynthetic activity and breathing process.

All the above results in the existence of damaged plants requiring compounds or substances that not only help to prevent dehydration conditions, but in addition help the plants to recover from the bath health in a few time, since in case of a non opportune action, the plants may become more deteriorated.

On the other hand, the plants also suffer diseases and are attacked by pests, such as the white fly being a very common pest in greenhouse cultures and even in the field, further, the white fly transmits viral infections damaging the plants in great extent.

To all the above mentioned factors causing plant damage or stress, the damage caused by man may be added, when he does not properly manage the plants in the greenhouses or in the culture fields.

The above problems results in the prior art development of compositions trying to protect the plants against some of these factors causing stress, such as the composition described in the U.S. Pat. No. 4,094,845, which is directed to provide a water loss reducing composition in the existing leaves and stems of plants by transpiration, besides, it has a protection effect against damages caused by the wind and cold. More specifically, the composition consists essentially of an aqueous solution or dispersion of a carboxilated hydrophilic acrylic polymer, a cross-linking agent for said polymer and an effective amount of UV rays absorption agent. The main feature of this composition is that have effect only to avoid water loosing, then having a limited application. In addition, it does not mention if a dehydrated plant can recover from this bad state.

On the other hand, with reference to protective compositions against pests, it can be cited the Mexican Patent application No. PA/a/2000/001970, which describes a composition comprising iodine or a iodine compound containing, having, generating or releasing molecular iodine; said composition may also contain additional secondary active ingredients, such as fertilizers, nutrients, micronutrients, promoters, polyasparts, herbicides, fungicides, etc., however, some of these components may damage other animal species or human if an inappropriate application thereof is carried out. Furthermore, having a composition with many substances increase the cost for obvious reasons.

As may be seen from the above, there is currently a lack of compositions which, with a few components, be highly effective for the protection of plants against several biotic or abiotic factors generating stress in plants, and above all, there is no composition which immediately improves, in a few time, the plants health. In this regard, it is known that any kind of fertilizers help to improve the plants health but with a very low action, such that the benefits from the fertilizers cannot be perceived immediately. Besides, most of the compositions have an agricultural main use, leaving aside people liking gardening.

SUMMARY OF THE INVENTION

As a consequence from the above, it has been looking for suppressing the existing problems for the protection and strengthening of plants, in such a manner that it has been found that a composition comprising polyethylene glycol, vitamin A or a derivative or precursor thereof, including mixtures of same, and at least a red coloring agent, all components having a synergistic effect providing a protection and strengthening effect on plants, pointing out particularly a readily and surprisingly strengthening of the plants having stress conditions. Further, the compositions protect the plants from the stress through their growing and development. More precisely the aqueous composition for the protection and strengthening of plants of the present invention comprises:
  a) polyethylene glycol in a concentration of about 2.0 to about 10.0 grams per liter of the composition, wherein the polyethylene glycol has a molecular weight of about 6000 to about 8000 grams/mol;
  b) vitamin A, or a derivative or precursor thereof, including mixtures of same, in a concentration of about 0.1 to about 10.0 grams per liter of the composition; and,
  c) at least a red coloring agent in a concentration of about 0.1 to about 10.0 grams per liter of the composition, wherein said coloring agent enables the passage of light at wavelengths greater than 600 nanometers.

In a preferred embodiment of the present invention, the vitamin A (retinol) derivative is selected from vitamin A acetate or vitamin A palmitate, while the precursor is selected from carotenoids. The red coloring agent is preferably a food grade coloring agent.

In a first embodiment of the present invention, the aqueous composition for the protection and strengthening of plants further comprises: (d) at least a glucoside in a concentration of about 0.5 to about 15 milligrams per liter of the composition; and/or (e) at least a foliar fertilizer.

Regarding the composition application method of the present invention, it comprises at least it: (a) providing a plant; and (b) applying the composition onto the leaves of the plant in an application dose of about 0.03 to about 0.05 ml per $cm^2$ of leaf of the plant, preferably, the application is made onto the upper side of the leaf or bundle receiving the sun light. As a preferred embodiment of the method of the present invention, the application is carried out by mechanical or manual spraying.

The composition of the present invention has outstanding effects when applied to plants obtained by micro-propagation going from in vitro conditions to ex vitro conditions, which are very susceptible to suffer stress, however, it can also be applied to plants obtained by conventional methods used in greenhouses.

In addition, an object of the present invention is to provide a protection and strengthening composition for plants, easy to obtain and to apply, and further having a lower cost compared with current compositions and fertilizers. A further object of the present invention is to provide a composition for the protection and strengthening of plants being innocuous for the man and other animal species.

BRIEF DESCRIPTION OF THE DRAWINGS

The novel aspects considered characteristics of the present invention are set forth particularly in the appended claims. However, the invention itself, both for its organization and for its application method, together with other objects and advantages thereof, will be better understood in the following detailed description of certain specific embodiments, when read in relation with the accompanying drawings, wherein:

DETAILED DESCRIPTION OF THE INVENTION

Figure 1A:
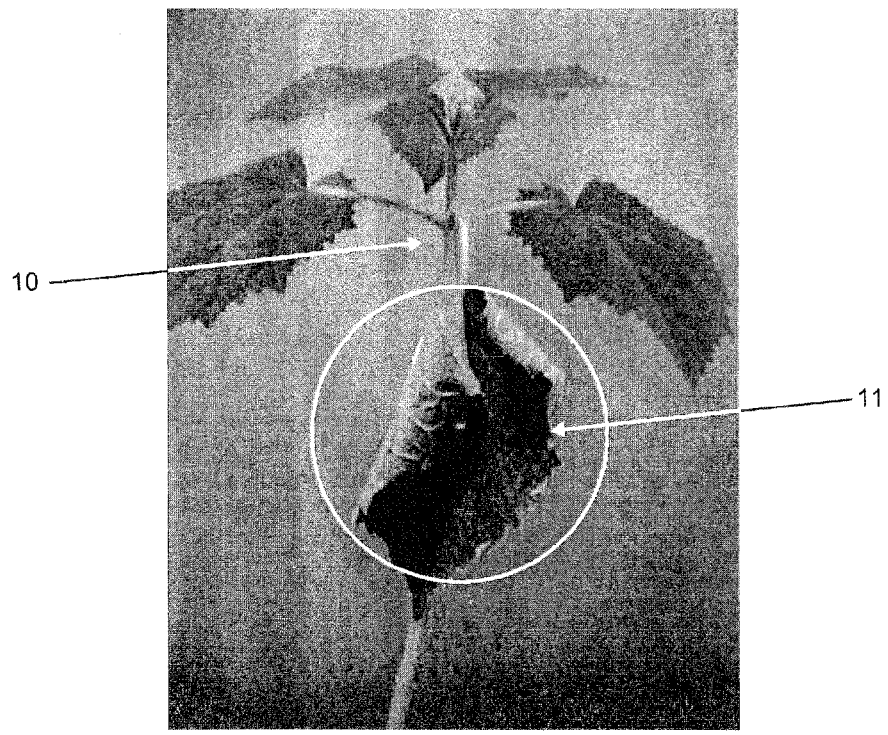
FIG. 1A is a side, bottom, perspective view of a plant of the species Paulownia elongata showing withered leaves due to a bad management in the greenhouse.

It has been found that an aqueous composition comprising: polyethylene glycol, vitamin A or a derivative or precursor thereof, including mixtures thereof, and at least a red coloring agent, has a synergistic effect over its components that, when applied onto the plants, brings protection against factors causing stress to the plants that are in this state. The aqueous composition of the present invention more particularly comprises the following:

a) polyethylene glycol in a concentration from about 2.0 to about 10.0 grams per liter of the composition, wherein the polyethylene glycol has a molecular weight of about 6000 to about 8000 grams/mol;

b) vitamin A or a derivative or precursor thereof, including mixtures of same, in a concentration of about 0.1 to about 10.0 grams per liter of the composition; and, c) at least a red coloring agent in a concentration of about 0.1 to about 10.0 grams per liter of the composition, wherein said coloring agent enables the passage of the light at wavelengths greater than 600 nanometers.

With regard to the above, it can be mentioned that, with respect to the polyethylene glycol molecular weight, lower than the limits of the indicated ratio, the weight concentration of this component would be necessarily higher, it is to say, a great amount of this component would have to be used in the composition. On the other hand, if the polyethylene glycol molecular weight is higher than the ratio upper limit, it is very difficult to dissolve it in the aqueous media.

It is convenient to mention that the polyethylene glycol function within the composition is to act as adherent of the same over the leaves of the plants onto which it is applied, besides, the polyethylene glycol forms a transparent film reducing the water loss of the leaf by transpiration, as a result of the plant photosynthesis and breathing.

Regarding the vitamin A derivative, the same is selected between vitamin A acetate or vitamin A palmitate, while the precursor is selected from carotenoids, in a preferred manner, from beta-carotene, zeaxanthine and lutheine. Vitamin A and derivatives and precursors thereof have the function of avoiding the photo-oxidation and to counteract the noxious dehydration effect caused by the lack or loss of water, winds at high speed or other factors also causing this problem, further giving the plant heat resistance.

Regarding the red coloring agent, the same is preferably selected among food grade coloring agents with the purpose that the composition be easily manufactured and not to represent prejudicial effects to animal species, including humans. In a preferred manner, in the aqueous composition, a red coloring agent 3, a red coloring agent 40, or a mixture thereof is used. The main function of the red coloring agent is to form a film on the leaf surface which enables the passage of light at wavelengths greater than about 600 nm, thus avoiding the wavelengths corresponding to UV rays, which, as it is well known, cause great damage to living beings.

Describing a first embodiment of the present invention, the protection and strengthening aqueous solution for plants further comprises; (d) at least a glucoside in a concentration of about 0.5 to about 15 mg per liter of the composition, and/or, (e) at least a foliar fertilizer. From these, the glucosidal functions as a natural agent against pathogen microorganisms and insects, besides to function as an stimulant for lignin production, being a compound giving consistency and strengthening to the plant cells, and as a consequence to the tissues, in a preferred manner said glucoside is selected from the following glucosides: phloridzin (phloretin-2-β-D-glucoside) phloretin (β-(4-hydroxyphenyl)-2,4,6,-trihydroxypropiophenone), quercetin (3,3',4',5,6-pentahydroxyflavone), rutoside (quecetin-3-rutinoside) or phloroglucinol (1,3,5-trihydroxybencene), in a preferred manner, the glucoside used in the invention is phloridzin.

Regarding the foliar fertilizers, these are widely used in the technical field, and among its main ingredients are the nitrogen, phosphorous and potassium compounds enriched with minerals such as chrome, iron, sulfur, zinc, calcium, magnesium; examples of these foliar fertilizers are those known under the commercial trademarks COSMOCEL 20-30-10®, TRICEL-20® and Bayfolan Forte®, these fertilizers are added to the aqueous composition according to the respective manufacturers recommended doses, it is worth to insist in the fact that the addition of this kind of fertilizers to the composition of the present invention is optional, since as it may be observed in the examples, the same has benefic effects either without the inclusion of these foliar fertilizers.

The pH of the aqueous composition for the protection and strengthening of plants of the present invention is between about 3.5 to about 7.0.

Regarding the application method for the aqueous composition for the protection and strengthening of plants of the present invention, said method comprises the following steps:

a) providing a plant; and,
b) applying the composition onto the leaves of the plant in an application dose of about 0.03 to about 0.05 ml per $cm^2$ of plant leaf.

With regard to the above, in a preferred embodiment of this method, the application is made over the upper side of the leaf (bundle) receiving the sun light or other source of light. The application dose in the indicated ratio permits to cover satisfactory the hole leaf surface onto which the composition is being applied, out of the pointed ratio, the leaf would not be satisfactory covered, or the composition would be excessively applied.

In another application method embodiment of the present invention, the same is realized by mechanical or manual spraying such that the application may be easily made by the greenhouse or culture field personnel, or by people having liking for gardening.

In a more preferred manner, the aqueous composition of the present invention is applied to plants obtained by micro-propagation going from in vitro conditions to ex vitro conditions, wherein it is known by the skilled in the art that plants suffer stress by a sudden greater light intensity receipt and by a sudden decrease of the environment relative humidity. However, the composition of the present invention may also be applied to small leaf clusters obtained by conventional seeds and cuttings methods, without being important the plant gender or species, such as vegetables, ornamental plants, etc.

The application of the present invention composition can be carried out at any time of the plant life, and the application may be repeated as required thereby.

The aqueous composition for the protection and strengthening of plants, as well as its application method will be more clearly illustrated by the following specific examples described below, which are only illustrative but not limitative of the invention, being said examples as follows:

Example 1

Preparation of the Composition

In a 1 L beaker with 500 ml bi-distillated water, 5 g of polyethylene glycol were dissolved under constant stirring, the molecular weight of the polyethylene glycol was 6000 grams/mol, further the following compounds were added one by one to the beaker: 0.5 g of pharmaceutical grade vitamin A palmitate for human use; and 0.5 g of red coloring agent under the trademark "Masterchef", which is a food grade coloring agent used in bakery, consisting of a mixture of red coloring agent 3 and red coloring agent 40. Finally, a sufficient amount of water was added to the beaker to complete a liter.

Example 2

Application to Bad Managed Stressed Plants

Figure 1B:
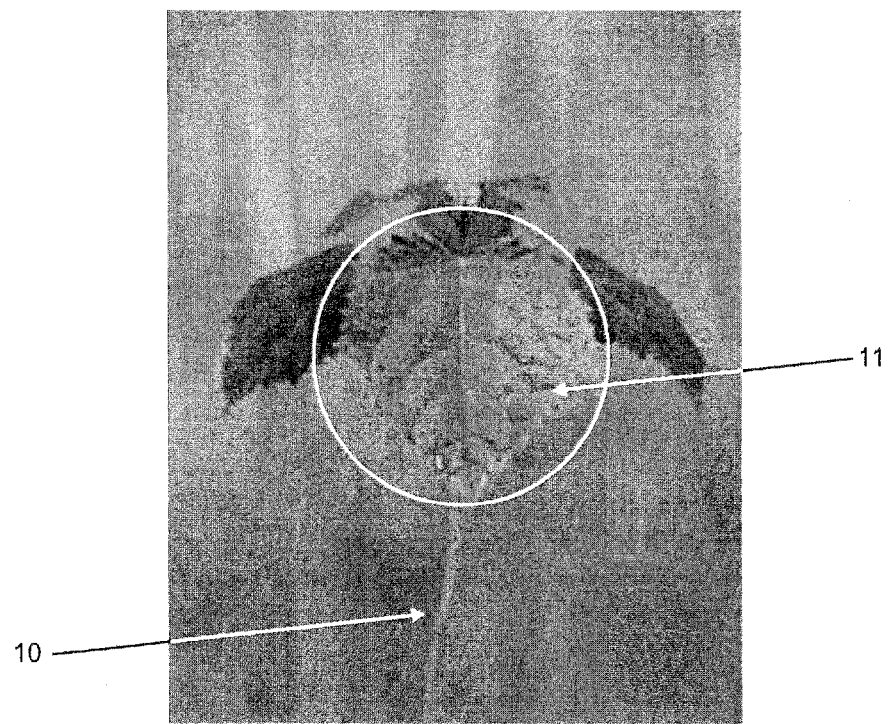
FIG. 1B is a bottom, side, perspective view of the same plant showed in FIG. 1A after 60 minutes from the receipt of the application of the aqueous composition of the present invention formulated according to a specific embodiment thereof.

In order to explain this example, reference to FIGS. 1A and 1B is made. Specifically, FIG. 1A shows a plant 10 of the species *Paulownia elongata* of 4 weeks of life, the plant showed stress due to a bad management in the greenhouse, as a notorious evidence of the plant stress one of its leafs was completely withered, this leaf is clearly identified in FIG. 1A within a circle and the 11 numeric reference.

With the object of improving the plant condition, the composition obtained in the example 1 was applied to the upper side of all the leafs of the plant, with an application dose of 0.05 ml per $cm^2$ of the leaf. After 60 minutes from the application, the plant 10 showed a surprisingly and non-expected improvement, in a more surprisingly manner it was observed the total recovery of the leaf 11. This can be clearly appreciated in FIG. 1B.

Example 3

Application in Plants Obtained by Micro-Propagation

In order to study the effect of the composition of the present invention over plants obtained by micro-propagation, which goes from in vitro conditions to ex vitro conditions, two study groups of a species *Paulownia elongata* were formed. The composition prepared according to the example 1 was applied to the first group every 15 days, while the second group was not applied with the composition, i.e., it was a control group. After 45 days and three applications at 0, 15 and 30 days, the first group of plants showed a greater size than the second group of plants, further, showed great force and an intense green color as indicatives of having a good photosynthesis. All this was interpreted as a good adaptation of the plants to the ex vitro conditions. Contrariwise, the second group of plants showed a pale green or yellowish color, with less vegetative development, in other words, they showed less number of leaves and smaller size thereof compared to the leaves of the first group of plants.

Example 4

Culture Field Studies of Plants Previously Treated with the Composition in the Greenhouse Some of the first group of plants, as well as others from the second group mentioned in the example 3 were transplanted to a culture field, wherein were treated under the same environment and watering conditions. After 6 months of said transplant, the plants of this group being treated with the composition of the present invention showed an important vegetative development and a normal development of the apical meristem of the plant, on the contrary, the plants not treated showed a smaller size and a non-efficient leaves development.

Example 5

Application of the Composition to Greenhouse Small Leaf Clusters

In order to determine the effect of the composition of the present invention applied to greenhouse tomato small leaf clusters of the "saladet" variety, 5 study groups were formed identified as follows:

1) C, a control group not receiving the composition of the present invention;
2) R1, a group to which the composition prepared according to the example 1 was applied, adding 3.0 ml/l of foliar fertilizer of the commercial trademark "Bayfolan Forte" and 3 mg of phloridzin (glucoside);
3) R2 a group to which the composition prepared according to the example 1 was applied, incorporating 3 mg of phloridzin in the above mentioned fertilizer;
4) R3 a group to which the composition prepared according to the example 1 was applied, i.e., without foliar fertilizer and without glucoside;
5) R4, a group to which the composition prepared according to the example 1 was applied, with 3 ml/l of foliar fertilizer of the commercial trademark "Bayfolan Forte".

In groups R1 to R4 the composition was applied in an application dose of 0.05 ml per $cm^2$ of the leaf, such that all the upper surface of the leaf of the plant was covered.

The variable studied in the plants was the height in cm, after 3 applications in 45 days.

Figure 2:
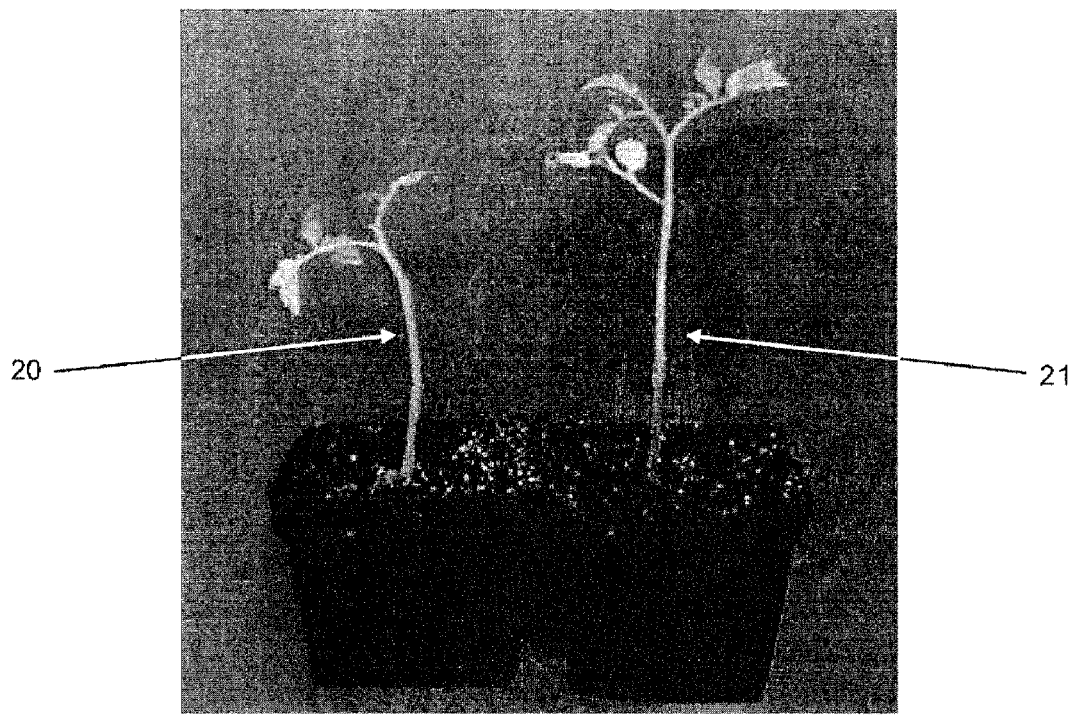
FIG. 2 is a comparative view showing two small leaf clusters of the "saladet" variety, cultured under the same greenhouse conditions, one of them having being treated with the composition of the present invention.
Figure 3:
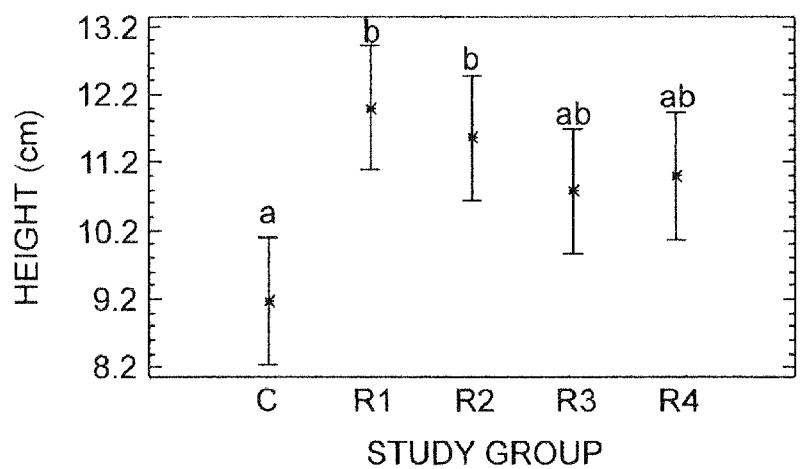
FIG. 3 is a graphic showing the results obtained from a multiple media analysis, from height measurements carried out over study groups formed by small leaf clusters of "saladet" tomato obtained in a greenhouse, to which, except to one group, the composition of the present invention formulated according to specific embodiments thereof was applied

In an variance statistics analysis ($\alpha=0.05$) it was observed the existence of a significant difference between groups R1 to R4 with respect to the control group C, resulting in the conducting of a multiple media comparative analysis shown in FIG. 3, wherein it is important to point out that averages with the same letter are not significantly different. In FIG. 3, the existence of very important differences between groups R1 and R2 with respect to the control group C, to which the composition was not applied, such that in this development phase of the plants, the composition used in groups R1 and R2 favors a better growing of the plants. In order to make the above more evident, reference to FIG. 2 is made, wherein a plant 20 of the control group C is shown compared to another plant belonging to the R1 group, wherein the height difference therebetween is evident.

Example 6

Application to Small Leaf Clusters Transplanted to a Culture Field

The same study groups as in example 5 were formed of the same age small leaf clusters, from the same tomato variety, but transplanted to soil, the response varieties were the plant height and stem diameter at the base thereof, said variables were measured after 4 applications and 65 days after the transplanting in the field.

Figure 4:
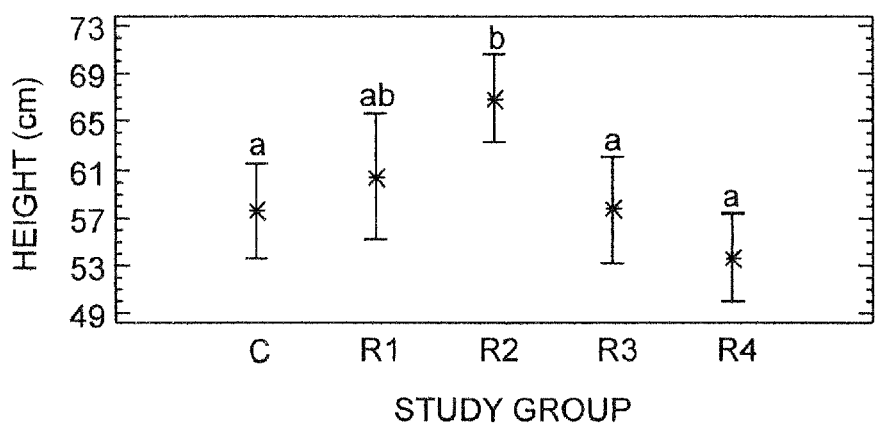
FIG. 4 is a graphic showing the results obtained in a multiple media analysis from height measurements carried out over study groups formed by small leaf clusters of "saladet" tomato transplanted to field, to which except to one group, the composition of the present invention, formulated according to specific embodiments thereof was applied.

Regarding the height variable, the variance analysis showed the existence of o significant difference ($\alpha=0.05$) in the different groups, leading to carry out a multiple average comparative test, shown in FIG. 4, wherein it is important to mention that averages with the same letter are not significantly different. In FIG. 4, it was observed a significant existence between the group of plants R2 which received the treatment and the control group, concluding that at least in this development phase, the plants of R2 treated with the formulation showed a bigger size with respect to the plants of the control group C.

Figure 5:
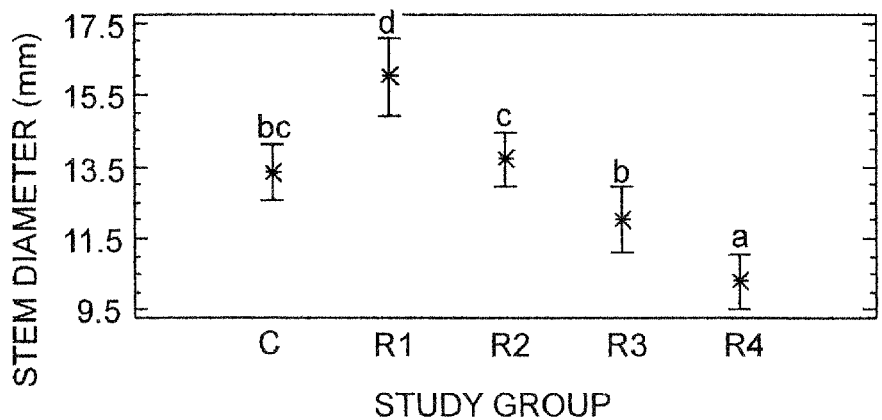
FIG. 5 is a graphic showing the results obtained in a multiple media analysis from measurements of the stem base diameter conducted over the same study groups of FIG. 4.

Regarding the stem diameter variable, the variance analysis showed the existence of a significant difference ($\alpha=0.05$), also leading to carry out a multiple average comparative test shown in FIG. 5, wherein it is important to mention that averages with the same letter are not significantly different. In FIG. 5, it was observed a significant existence between the group of plants of R1 which received the treatment and the control group, concluding that at least in this development phase, the plants of R1 treated with the formulation showed a bigger diameter with respect to the plants of the control group.

Although in the above description reference to certain embodiments of the present invention has been made, it must be emphasized that several modifications to all embodiments are possible, such as the coloring agent selection, or the selection of the vitamin A derivative or precursor or the glucoside selection as phloridzin, but without departing from the scope of the invention. Therefore, the present invention must not be restricted except for the set forth in the prior art and the appended claims.

What is claimed is:

1. An aqueous composition for the protection and strengthening of plants comprising:
   a) polyethylene glycol in a concentration from about 2.0 to about 10.0 grams per liter of the composition, wherein the polyethylene glycol has a molecular weight of about 6000 to about 8000 grams/mol;
   b) vitamin A or a derivative or precursor thereof, including mixtures of same, in a concentration of about 0.1 to about 10.0 grams per liter of the composition; and,
   c) at least a red coloring agent in a concentration of about 0.1 to about 10.0 grams per liter of the composition;
   wherein said coloring agent enables the passage of light at wavelengths greater than 600 nanometers;
   wherein the vitamin A derivative is selected from the group consisting of vitamin A acetate and vitamin A palmitate.

2. The aqueous composition for the protection and strengthening of plants, according to claim 1, wherein the vitamin A precursor is a carotenoid.

3. The aqueous composition for the protection and strengthening of plants, according to claim 2, wherein the carotenoid is selected from the group consisting of beta-carotene, zeaxanthine and lutheine.

4. The aqueous composition for the protection and strengthening of plants, according to claim 1, wherein the red coloring agent is a food grade coloring agent.

5. The aqueous composition for the protection and strengthening of plants, according to claim 4, wherein the red coloring agent is selected from the group comprising red 3 coloring agent, red 40 coloring agent or a mixture thereof.

6. An aqueous composition for the protection and strengthening of plants comprising:
   a) polyethylene glycol in a concentration from about 2.0 to about 10.0 grams per liter of the composition, wherein the polyethylene glycol has a molecular weight of about 6000 to about 8000 grams/mol;
   b) vitamin A or a derivative or precursor thereof, including mixtures of same, in a concentration of about 0.1 to about 10.0 grams per liter of the composition; and,
   c) at least a red coloring agent in a concentration of about 0.1 to about 10.0 grams per liter of the composition;
   wherein said coloring agent enables the passage of light at wavelengths greater than 600 nanometers;
   d) at least a glucoside in a concentration from 0.5 to 15 mg per liter of the composition; and
   e) at least a foliar fertilizer.

7. The aqueous composition for the protection and strengthening of plants according to claim 6, wherein said glucoside is selected from the group comprising phloridzin (phloretin-2-β-D-glucoside); phloretin (β-(4-hydroxyphenyl)-2,4,6,trihydroxypropiophenone), quercetin (3,3',4',5,6-pentahydroxyflavone), rutoside (quercetin-3-rutinoside) and phloroglucinol (1,3,5-trihydroxybencene).

8. The aqueous composition for the protection and strengthening of plants according to claim 7, wherein said glucoside is phloridzin.

9. The aqueous composition for the protection and strengthening of plants according to claim 1, further having a pH from 3.5 to 7.0.

10. A method for the protection and strengthening of plants comprising the steps of:
 a) providing a plant;
 b) applying a composition onto the leaves of the plant in an application dose of about 0.03 to about 0.05 ml per cm2 of the leaf of the plant;
 wherein the composition is an aqueous composition for the protection and strengthening of plants including: a) polyethylene glycol in a concentration from about 2.0 to about 10.0 grams per liter of the composition, wherein the polyethylene glycol has a molecular weight of about 6000 to about 8000 grams/mol; b) vitamin A or a derivative or precursor thereof, including mixtures of same, in a concentration of about 0.1 to about 10.0 grams per liter of the composition; and c) at least a red coloring agent in a concentration of about 0.1 to about 10.0 grams per liter of the composition; wherein said coloring agent enables the passage of light at wavelengths greater than 600 nanometers; and
 wherein the application is carried out by mechanical or manual spraying.

11. The method according to claim 10, wherein the application is carried out onto the upper side of the leaf of the plant.

12. A method for the protection and strengthening of plants comprising the steps of:
 a) providing a plant; and,
 b) applying a composition onto the leaves of the plant in an application dose of about 0.03 to about 0.05 ml per cm2 of the leaf of the plant;
 wherein the composition is an aqueous composition for the protection and strengthening of plants including: a) polyethylene glycol in a concentration from about 2.0 to about 10.0 grams per liter of the composition, wherein the polyethylene glycol has a molecular weight of about 6000 to about 8000 grams/mol; b) vitamin A or a derivative or precursor thereof, including mixtures of same, in a concentration of about 0.1 to about 10.0 grams per liter of the composition; and c) at least a red coloring agent in a concentration of about 0.1 to about 10.0 grams per liter of the composition; wherein said coloring agent enables the passage of light at wavelengths greater than 600 nanometers;
 wherein the composition is applied to plants obtained by micro-propagation going from in vitro conditions to ex vitro conditions.

13. A method for the protection and strengthening of plants comprising the steps of:
 a) providing a plant; and,
 b) applying a composition onto the leaves of the plant in an application dose of about 0.03 to about 0.05 ml per cm2 of the leaf of the plant;
 wherein the composition is an aqueous composition for the protection and strengthening of plants including: a) polyethylene glycol in a concentration from about 2.0 to about 10.0 grams per liter of the composition, wherein the polyethylene glycol has a molecular weight of about 6000 to about 8000 grams/mol; b) vitamin A or a derivative or precursor thereof, including mixtures of same, in a concentration of about 0.1 to about 10.0 grams per liter of the composition; and c) at least a red coloring agent in a concentration of about 0.1 to about 10.0 grams per liter of the composition; wherein said coloring agent enables the passage of light at wavelengths greater than 600 nanometers;
 wherein the composition is applied to small leaf clusters obtained by seed germination and cuttings methods.

\* \* \* \* \*